United States Patent [19]

Kluger et al.

[11] 4,374,068
[45] Feb. 15, 1983

[54] PROCESS FOR HYDROXYALKYLATION OF CYANOETHYLANILINES

[75] Inventors: Edward W. Kluger, Pauline; Jack L. Rolen, Inman, both of S.C.

[73] Assignee: Milliken Research Corporation, Spartanburg, S.C.

[21] Appl. No.: 311,661

[22] Filed: Oct. 15, 1981

[51] Int. Cl.$^3$ .......................................... C07C 121/80
[52] U.S. Cl. .............................. 260/465 D; 260/465 E
[58] Field of Search ....................... 260/465 E, 465 D

[56] References Cited

U.S. PATENT DOCUMENTS 3,766,240 10/1973 Sayigh ............................. 260/465 E

OTHER PUBLICATIONS

Pfeifer et al., Chemical Abstracts, vol. 76, 24934c, (1972).
Koch et al., Chemical Abstracts, vol. 78, 125813j, (1973).

Primary Examiner—Dolph H. Torrence
Attorney, Agent, or Firm—H. William Petry; Terry T. Moyer

[57] ABSTRACT

A process is provided for hydroxyalkylation of cyanoethylanilines, which comprises reacting an alkylene oxide of the formula:

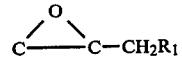

wherein $R_1$ is selected from H, Cl, Br, OH, a lower alkyl group containing from 1 to about 4 carbon atoms, or phenyl with a cyanoethyl aniline in a molar ratio of from about 1:1 to about 2:1 in a reaction medium at a temperature of from about 40° C. to about 130° C. in the presence of an acid catalyst provided in an amount sufficient to catalyze said reaction to thereby provide the corresponding hydroxyalkylated cyanoethyl aniline.

12 Claims, No Drawings

PROCESS FOR HYDROXYALKYLATION OF CYANOETHYLANILINES

The present invention relates to the catalytic hydroxyalkylation of cyanoethylanilines to provide the corresponding hydroxyalkylcyanoethylaniline reaction products which are useful as dyestuff intermediates.

It is known that cyanoethylhydroxyalkylanilines (herein CEHAA) and their acetylated derivatives, cyanoethylacyloxyalkylanilines (herein CEAAA) are useful as dyestuff intermediates, particularly as dye couplers for disperse dyestuffs. These compounds are said to combine good tinctorial power, affinity and fastness properties on both acetate and polyesters.

In general the dyestuff maker must employ these compounds in high purities, e.g., 90 percent or better, to prepare a dyestuff product. The use of these compounds as intermediates in impure form may result in processing problems or in undesirable properties of the final product such as tarring, poor yield, color problems, sublimation and poor fastness properties.

With regard to the synthesis routes which are presently available for the preparation of CEHAA compounds, typically the yields achieved may be relatively low, and the removal of impurities, such as unreacted starting materials, and other undesired by-products may be required.

Accordingly, it would be highly desirable to provide a process whereby CEHAA compounds and their acetylated derivatives may be prepared in high yields using moderate reaction conditions and with minimal formation of undesired by-products.

According to the present invention a process is provided for the preparation of CEHAA compounds which comprises reacting an alkylene oxide of the formula:

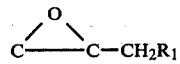

wherein $R_1$ is selected from H, Cl, Br, OH, a lower alkyl group containing from 1 to about 4 carbon atoms, or phenyl with a cyanoethylaniline in a molar ratio of from about 1:1 to about 2:1 in a reaction medium at a temperature of from about 40° C. to about 130° C. in the presence of an acid catalyst provided in an amount sufficient to catalyze said reaction to thereby provide the corresponding hydroxyalkylated cyanoethylaniline.

According to the present invention a wide variety of CEHAA compounds may be prepared in high yields and with minimal formation of undesired byproducts at moderate reaction conditions. Preferred CEHAA compounds may be represented by the following structural formula:

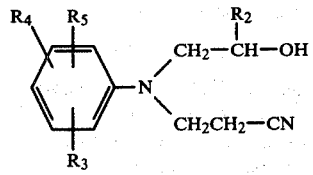

wherein $R_2$ is selected from H, Cl, Br, OH, a lower alkyl group containing from 1 to about 4 carbon atoms, or phenyl; and $R_3$, $R_4$ and $R_5$ are each independently selected from H, a lower alkyl group containing from 1 to about 4 carbon atoms, halogen, $NO_2$, OH, a lower alkoxy group containing from 1 to about 4 carbon atoms, and $NHCOR_6$ where $R_6$ is H or a lower alkyl group containing from 1 to about 4 carbon atoms. The most preferred CEHAA compound which may be prepared according to the present invention is cyanoethylhydroxyethylaniline (CEHEA).

The temperature at which the above described alkoxylation may be carried out may vary widely. Generally, however, the temperature may be within a range of from about 40°–130° C. and preferably in the range of about 50°–100° C. Likewise, the period of time required for the reaction to go to substantial completion may vary widely, such being dependent on alkylene oxide addition pressure, alkylene oxide concentration, the type of acid catalyst, the amount of acid catalyst and whether or not a solvent is used. Generally, however, the reaction proceeds to completion when the reactants are contacted at the desired temperature in about 0.2 to about 8 hours. The alkylene oxide addition pressures in the range of 1 to about 70 psi can be used to accomplish the hydroxyalkylation reaction. Nitrogen pressure ranging from 0 to about 15 psi can also be used. While alkylene oxide pressures in the higher range, 50–70 psi, can be used and may be advantageous, lower pressures, 5–15 psi, can also be used without any particular difficulty. The amount of alkylene oxide used may vary from stoichiometric to about a 2 molar excess. Preferably about 1.1 to 1.3 moles of alkylene oxide are used per 1 mole of cyanoethylated aniline to avoid alkyl glycol formation and over alkoxylation in general.

The hydroxyalkylation of cyanoethylanilines may be carried out in the presence or absence of a solvent or water. When a solvent is employed, any suitable solvent which will not interfere with the desired hydroxyalkylation can be employed, such as, cycloaliphatic ethers, e.g., dioxane, tetrahydrofuran, and the like, and high boiling hydrocarbons, e.g., hexane, cyclohexane, heptane, decane, toluene, xylenes, and the like.

In carrying out the hydroxyalkylation of cyanoethylated anilines any suitable acid catalyst can be employed. Typical of such acid catalysts are organic carboxylic acids such as acetic, formic and propionic acids, and other organic acids, e.g., paratoluene sulfonic, methane sulfonic acid and polymeric acidic ion exchange resins thereof, e.g., A-15 made by Dow which is a sulfonated polystyrene, and mineral acids such as phosphoric, hydrochloric, sulfuric and the like and Lewis acids and/or salts, e.g., zinc chloride or halides, iron halides, copper halides, nickel halides, boron trifluoride, and other boron halides either complexed or in the free state. While inorganic acids and salts work equally as well as organic acid catalysts, organic acid catalysts do not lead to any purification and potential corrosion problems. The preferred acid catalyst is acetic acid since it can readily be removed by vacuum stripping and can also coform the desired cyanoethylacyloxyalkylaniline final product thereby reducing thhe amount of acyl anhydrides required to convert the cyanoethylhydroxyalkylaniline intermediate present. The amount of catalyst employed in the acid catalyzed process can vary widely. However, generally the amount of catalyst will vary from 0.1 percent to 30 percent weight percent, and preferably from about 1 to 10 percent weight percent.

A preferred embodiment of the present invention will be described with particular reference to the preferred product CEHEA although it is to be understood that the invention is not to be limited thereby. In accordance with this preferred embodiment, CEHEA is produced by the ethoxylation of cyanoethylaniline. The ethoxylation may be typically accomplished by adding ethylene oxide into a reaction vessel containing cyanoethylaniline, either in the presence or absence of a solvent or water and an acid catalyst. The corresponding CEHEA is selectively produced in high yield and purity as shown in equation 2 below:

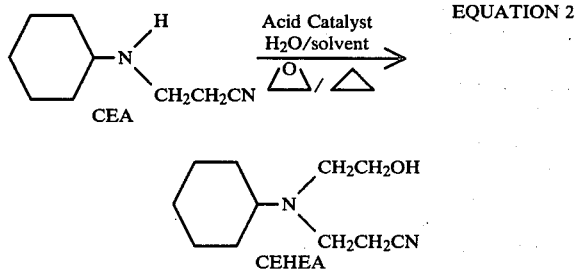

When an organic carboxylic acid is employed as a catalyst it may actually enter into the reaction and result in coformation of CEAEA product as shown in Equation 3 below:

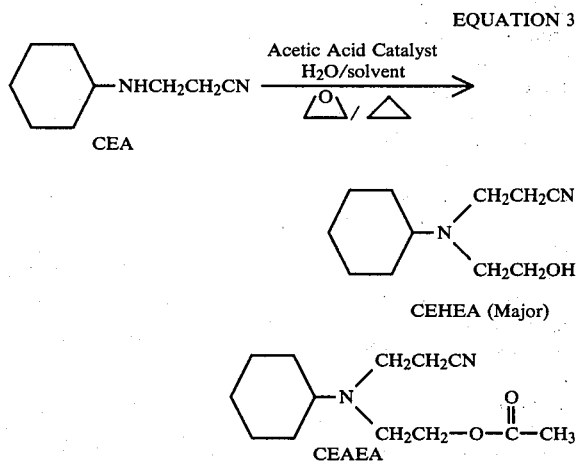

Far from being detrimental, the presence of CEAEA in the reaction product may be desired since in many end use applications the primary product of the reaction, namely CEHEA, may be subjected to acetylation to make the corresponding CEAEA as a final product. In general, the formation of CEAEA may be favored by increasing somewhat the reaction temperature and reaction time.

In the following examples which are not to be construed as unduly limiting the invention all parts and percentages are by weight unless otherwise indicated.

EXAMPLE 1

This examples illustrates the difficulties encountered in attempting to conduct the reaction with which the invention is concerned in the absence of an acid catalyst of the type disclosed herein. In a two liter stirred autoclave was charged 295 g (2.02 moles) of recrystallized cyanoethylaniline. The autoclave was then purged three times to 60 psi with nitrogen gas. The reaction was heated to 100° C. and pressured to 10 psi with nitrogen gas. Ethylene oxide was then added slowly to the autoclave under nitrogen pressure so that the maximum reaction pressure was about 60 psi. As the ethylene oxide was slowly reacted more was added. After three hours, 90 g (2.0 moles) of ethylene oxide was added to the reactor at 100° C. After an additional 2 hours at 100° C. about 35 percent of the cyanoethylaniline still remained in the product mixture. At this time an additional 30 g of ethylene oxide was then added to the autoclave. After an additional 2 hours at 100° C. about 30 percent of cyanoethylaniline still remained in the product mixture. The temperature was then gradually increased to about 130° C. and an additional 30 g of ethylene oxide was added. The reaction mixture was post heated at 120° C. for an additional 5 hours. Afterwards, the volatiles were stripped away at 15–20 mmHg and the autoclave was cooled down and the contents were emptied. A GLC analysis of the crude reaction mixture showed it to contain 81 percent cyanoethylhydroxyethylaniline and 10 percent of cyanoethylaniline. This corresponds to a 90 percent conversion of the cyanoethylaniline and an 81 percent purity. An 83.7 g portion of this crude mixture was reacted with excess acetic anhydride at 70°–80° C. GLC analysis of the acetylated product showed it to contain the major components; 79 percent of cyanoethylacetoxyethylaniline, 10 percent of cyanoethylacetylaniline, and about 8 percent of polycyanoethylacetoxyethylaniline.

EXAMPLE 2

This example was conducted pursuant to the condition suggested by Pfeifer CA 76 24934C (at 100° C.) and illustrates the low conversion rate achieved using a non-catalyzed system. In a two liter stirred autoclave was charged 942 g (6.45 moles) of recrystallized cyanoethylaniline and 116 g of water. The autoclave was then purged three times to 60 psi with nitrogen gas. The reactor was heated to 100° C. and pressured to 10 psi with nitrogen gas. Ethylene oxide was then slowly added to the autoclave under nitrogen pressure so that the maximum reactor pressure was about 60 psi. As the ethylene oxide was slowly reacted, more was added. After nine hours, 345 g (7.84 moles) of ethylene oxide was added to the reactor at 100° C. The reaction mixture was post heated at 100° C. for an additional ten hours. Afterwards, the volatiles were stripped away at 15–20 mmHg and the autoclave was cooled down and the contents were emptied. A GLC analysis of the crude reaction showed it to contain 57 percent cyanoethylhydroxyethylaniline, and 42 percent cyanoethylaniline. This corresponds to a 58 percent conversion of cyanoethylaniline and a 57 percent purity. A 137.3 g portion of this crude mixture was reacted with excess acetic anhydride at 70°–80° C. GLC analysis of the acetylated product showed the major components 48 percent cyanoethylacetoxyethylaniline, 44 percent of cyanoethylacetylaniline, and 6 percent phenylethanolaminediacetate.

EXAMPLE 3

This example illustrates a reaction conducted at a higher temperature than that employed by Pfeifer (see Example 2) and shows a somewhat higher conversion rate with undesired oligomer formation as reported by Koch et al. CA 78 125813j. In a two liter stirred autoclave was charged 942 g (6.45 moles) of cyanoethylaniline and 116 g of water. The autoclave was then purged three times to 60 psi with nitrogen gas. The reactor was heated to 135°–140° C. and pressured to 10 psi with nitrogen gas. Ethylene oxide was then slowly added to the autoclave under nitrogen pressure so that the maximum reactor pressure was about 60 psi. As the ethylene oxide was slowly reacted, more was added. After nine hours 345 g (7.84 moles) of ethylene oxide was added to the reactor at 135°–140° C. The reaction mixture was post heated for an additional 8 hours at 135°–140° C. Afterwards, the volatiles were stripped away at 15–20 mmHg and the autoclave was cooled down and the contents were emptied. A GLC analysis of the crude reaction showed it to contain 74 percent cyanoethylhydroxyethylaniline, and 22.1 percent cyanoethylaniline. This corresponds to a 78 percent conversion of the cyanoethylaniline and a 74 percent purity. A 125.9 g portion of this crude mixture was reacted with excess acetic anhydride at 70°–80° C. GLC analysis of the acetylated product showed the major components; 68 percent cyanoethylacetoxyethylaniline, and 25.2 percent of cyanoethylacetylaniline.

EXAMPLE 4

Examples 4 through 11 illustrate the subject matter of the present invention showing different acid catalysts and starting materials.

In a two liter stirred autoclave was charged 942 g (6.42 moles) of cyanoethylaniline and 144 g of glacial acetic acid. The autoclave was then purged three times to 60 psi with nitrogen gas. The reaction mixture was heated to 70° C. and pressured to about 1 psi with nitrogen gas. Ethylene oxide was then slowly added to the autoclave at such a rate that maximum pressure did not exceed 15 psi and the maximum temperature did not exceed 100° C. As the ethylene oxide was slowly added the reaction exothermed. After two hours 345 g (7.84 moles) of ethylene oxide was added to the reactor such that the temperature was maintained below 100° C. The reaction mixture was post heated for an additional two hours at 80° C. Afterwards, the volatiles were stripped away at 15–20 mmHg and the autoclave was cooled down and the contents were emptied. An LC analysis of the crude reaction showed it to contain 93.8 percent cyanoethylhydroxyethylaniline, 1.3 percent of cyanoethylacetoxyethylaniline, and 1.0 percent cyanoethylaniline. This corresponds to a 99 percent conversion of the cyanoethylaniline and a 95.1 percent combined purity. A 105.3 g portion of this crude mixture was reacted with excess acetic anhydride at 70°–80° C. GLC analysis of the acetylated product showed it to contain 93.9 percent of cyanoethylacetoxyethylaniline and only 1.3 percent of the cyanoethylacetylaniline.

EXAMPLE 5

In a two liter stirred autoclave was charged 942 g (6.42 moles) of cyanoethylaniline and 151.2 g of acetic acid containing 4.8 percent water. The autoclave was then purged three times to 60 psi with nitrogen gas. The reaction mixture was then heated to 70° C. and pressured to about 1 psi with nitrogen gas. Ethylene oxide was then added slowly to the autoclave at such a rate that the maximum pressure did not exceed 15 psi and the maximum temperature did not exceed 100° C. As the ethylene oxide was slowly added the reaction exothermed. After two hours 345 g (7.84 moles) of ethylene oxide was added to the reaction such that the temperature was maintained below 100° C. The reaction mixture was post heated for an additional two hours at 80° C. Afterwards, the volatiles were stripped away at 15–20 mmHg and the contents were emptied. An LC analysis of the crude reaction showed it to contain 92.9 percent cyanoethylhydroxyethylaniline, 2.9 percent of cyanoethylacetoxyethylaniline, and 0.3 percent cyanoethylaniline. This corresponds to a 99.7 percent conversion of the cyanoethylaniline and a 95.8 percent combined purity. A 110.0 g portion of this crude mixture was reacted with excess acetic anhydride at 70°–80° C. GLC analysis of the acetylated product showed it to contain 92.8 percent of cyanoethylacetoxyethylaniline and only 1.1 percent of the cyanoethylacetylaniline.

EXAMPLE 6

In a two liter stirred autoclave was charged 942 g (6.42 moles) of cyanoethylaniline a 237.6 g of acetic acid containing 9 percent water. The autoclave was then purged three times to 60 psi with nitrogen gas. The reaction mixture was then heated to 70° C. and pressured to about 1 psi with nitrogen gas. Ethylene oxide was then added slowly to the autoclave at such a rate that the maximum pressure did not exceed 15 psi and the maximum temperature did not exceed 100° C. As the ethylene oxide was slowly added the reaction exothermed. After two hours 345 g (7.84 moles) of ethylene oxide was added to the reaction such that the temperature was maintained below 100° C. The reaction mixture was post heated for an additional two hours at 80° C. Afterwards, the volatiles were stripped away at 15–20 mmHg and the contents were emptied. An LC analysis of the crude reaction showed it to contain 80 percent cyanoethylhydroxyethylaniline, 12.6 percent of cyanoethylacetoxyethylaniline, and 1.4 percent cyanoethylaniline. This corresponds to a 98.6 percent conversion of the cyanoethylaniline and a 92.6 percent combined purity. A 117.3 g portion of this crude mixture was reacted with excess acetic anhydride at 70°–80° C. GLC analysis of the acetylated product showed it to contain 91.4 percent of cyanoethylacetoxyethylaniline and only 2.2 percent of the cyanoethylacetylaniline.

EXAMPLE 7

In a two liter stirred autoclave was charged 800 g (5.5 moles) of cyanoethylaniline and 68.1 g of an acetic acid solution containing 10 percent water. The autoclave was then purged three times to 60 psi with nitrogen gas. The reaction mixture was heated to 80° C. and pressured to about 1 psi with nitrogen gas. Propylene oxide was then slowly added to the autoclave at such a rate that the maximum temperature did not exceed 100° C. As the propylene oxide was slowly added the reaction exothermed. After three hours 400 g (6.9 moles) of propylene oxide was added to the reaction such that the temperature was maintained below 100° C. The reaction was post heated for an additional three hours at 80° C. Afterwards, the volatiles were stripped away at 15–20 mmHg and the autoclave was cooled and emptied. An LC analysis of the crude reaction showed it to contain 90.4 percent cyanoethylhydroxypropylaniline and 3 percent cyanoethylaniline corresponding to a 97 percent conversion of the cyanoethylaniline.

EXAMPLE 8

In a one gallon stirred autoclave was charged 1978 g (19.35 moles) of cyanoethylmetatoluidine and 167.2 g of acetic acid containing 10 percent water. The autoclave was then purged three times to 60 psi with nitrogen gas. The reaction mixture was heated to 80° C. and pressured to about 1 psi with nitrogen gas. Ethylene oxide was then slowly added to the autoclave at such a rate that the maximum pressure did not exceed 15 psi and the maximum temperature did not exceed 100° C. As the ethylene oxide was slowly added the reaction exothermed. After three hours 630 g (14.31 moles) of ethylene oxide was added to the reaction such that the temperature was maintained below 100° C. The reaction mixture was post heated for an additional three hours at 80° C. Afterwards, the volatiles were stripped away at 15-20 mmHg and the autoclave was cooled and emptied. An LC analysis of the crude reaction showed it to contain 94.6 percent cyanoethylhydroxyethylmetatoluidine and 1.2 percent cyanoethylmetatoluidine. This corresponds to a 98.8 percent conversion of the cyanoethylmetatoluidine. A 68 g portion of this crude mixture was reacted with excess acetic anhydride at 70°-80° C. GLC analysis of the acetylated product showed it to contain 93.2 percent of cyanoethylacetoxyethylmetatoluidine and only 0.9 percent of the cyanoethylacetylmetatoluidine.

EXAMPLE 9

In a two liter stirred autoclave was charged 800 g (5.5 moles) of cyanoethylaniline and 46 g of an aqueous solution containing 50 percent formic acid. The autoclave was then purged three times to 60 psi with nitrogen gas. The reaction mixture was then heated to 80° C. and pressured to about 1 psi with nitrogen gas. Ethylene oxide was then added slowly to the autoclave at such a rate that the maximum pressure did not exceed 15 psi and the maximum temperature did not exceed 100° C. As the ethylene oxide was slowly added the reaction exothermed. After five hours 350 g (7.95 moles) of ethylene oxide was added to the reaction such that the temperature was maintained below 100° C. The reaction mixture was post heated for an additional four hours at 80° C. Afterwards, the volatiles were stripped away at 15-20 mmHg and the contents were emptied. An LC analysis of the crude reaction showed it to contain 92.4 percent of cyanoethylhydroxyethylaniline, 1.9 percent of cyanoethylformoxyethylaniline, and 0.6 percent cyanoethylaniline. This corresponds to a 99.4 percent conversion of cyanoethylaniline and a 94.3 percent combined purity.

EXAMPLE 10

In a two liter stirred autoclave was charged 400 g (2.73 moles) of recrystallized cyanoethylaniline and 57 g of an aqueous solution containing 29.8 percent of a Lewis Acid, namely zinc chloride. The autoclave was then purged three times to 60 psi with nitrogen gas. The reaction mixture was then heated to 80° C. and pressured to about 1 psi with nitrogen gas. Ethylene oxide was then added slowly to the autoclave at such a rate that the maximum pressure did not exceed 15 psi and the maximum temperature did not exceed 100° C. As the ethylene oxide was slowly added the reaction exothermed. After three hours 220 g (5 moles) of ethylene oxide was added to the reaction such that the temperature was maintained below 100° C. The reaction mixture was post heated for an additional three hours at 80° C. Afterwards, the volatiles were stripped away at 15-20 mmHg and the contents were emptied. An LC analysis of the crude reaction showed it to contain 95.5 percent of cyanoethylhydroxyethylaniline and only 0.5 percent cyanoethylaniline. This corresponds to a 99.5 percent conversion of cyanoethylaniline. A 73.5 g portion of this crude mixture was reacted with excess acetic anhydride at 70°-80° C. A GLC analysis of the acetylated product showed it to contain 92.6 percent of cyanoethylacetoxyethylaniline and only 0.7 percent of cyanoethylacetylaniline.

EXAMPLE 11

In a two liter stirred autoclave was charged 800 g (5.5 moles) of cyanoethylaniline and 41.3 g of an aqueous solution containing 33.8 percent of a mineral acid $H_3PO_4$. The autoclave was then purged three times to 60 psi with nitrogen gas. The reaction mixture was then heated to 80° C. and pressured to about 1 psi with nitrogen gas. Ethylene oxide was then added slowly to the autoclave at such a rate that the maximum pressure did not exceed 15 psi and the maximum temperature did not exceed 100° C. As the ethylene oxide was slowly added the reaction exothermed. After four hours 440 g (10 moles) of ethylene oxide was added to the reaction such that the temperature was maintained below 100° C. The reaction mixture was post heated for an additional five hours at 80° C. Afterwards, the volatiles were stripped away at 15-20 mmHg and the contents were emptied. A GLC analysis of the crude reaction showed it to contain 94.6 percent cyanoethylhydroxyethylaniline and only 0.7 percent of cyanoethylaniline. This corresponds to a 99.3 percent conversion of cyanoethylaniline. A 76.2 g portion of this crude mixture was reacted with excess acetic anhydride at 70°-80° C. GLC analysis of the acetylated product showed it to contain 93.2 percent of cyanoethylacetoxyethylaniline and only 1.0 percent of cyanoethylacetylaniline.

What is claimed is:

1. A process for hydroxyalkylation of cyanoethylanilines which comprises reacting an alkylene oxide of the formula:

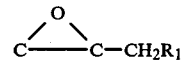

wherein $R_1$ is selected from H, Cl, Br, OH, a lower alkyl group containing from 1 to about 4 carbon atoms, or phenyl with a cyanoethylaniline in a molar ratio of from about 1:1 to about 2:1 in a reaction medium at a temperature of less than 100° C. in the presence of an acid catalyst provided in an amount sufficient to catalyze said reaction to thereby provide the corresponding hydroxyalkylated cyanoethylaniline.

2. The process of claim 1 wherein said cyanoethylanilines are represented by the following structural formula:

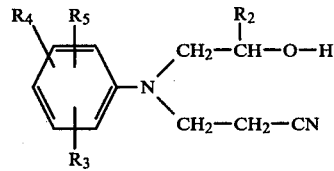

wherein $R_2$ is selected from H, Cl, Br, OH, a lower alkyl group containing from 1 to about 4 carbon atoms, or phenyl; and $R_3$, $R_4$ and $R_5$ are each independently selected from H, a lower alkyl group containing from 1 to about 4 carbon atoms, halogen, $NO_2$, OH, a lower alkoxy group containing from 1 to about 4 carbon atoms, and $NHCOR_6$ where $R_6$ is H or a lower alkyl group containing from 1 to about 4 carbon atoms.

3. The process of claim 1 wherein said reaction is performed for from about 0.2 to about 8 hours.

4. The process of claim 1 wherein said reaction is performed in the absence of a solvent.

5. The process of claim 1 wherein said reaction is performed in the presence of a solvent selected from water, cycloaliphatic ethers and high boiling hydrocarbons.

6. The process of claim 1 wherein said acid catalyst is an organic acid.

7. The process of claim 6 wherein said organic acid is selected from acetic, formic, propionic, paratoluenesulfonic or methanesulfonic acids.

8. The process of claim 7 wherein said acid is acetic acid.

9. The process of claim 1 wherein said acid catalyst is present in an amount of from about 1 percent to about 30 percent by weight.

10. The process of claim 1 wherein said acid catalyst is a Lewis acid.

11. The process of claim 1 wherein said Lewis acid is zinc chloride.

12. The process of claim 1 wherein said acid catalyst is a mineral acid catalyst.

* * * * *